US007980119B2

(12) United States Patent  (10) Patent No.: US 7,980,119 B2
Maeda et al.  (45) Date of Patent: Jul. 19, 2011

(54) AUTO-SAMPLER CLEANING MECHANISM

(75) Inventors: Yoshiaki Maeda, Kyoto (JP); Nobuyuki Tatsumi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 374 days.

(21) Appl. No.: 11/942,516

(22) Filed: Nov. 19, 2007

(65) Prior Publication Data

US 2008/0134804 A1  Jun. 12, 2008

(30) Foreign Application Priority Data

Dec. 6, 2006 (JP) .................................. 2006-328979

(51) Int. Cl.
*G01N 30/02* (2006.01)
(52) U.S. Cl. ......................... 73/61.56; 73/61.57; 422/70
(58) Field of Classification Search ............... 73/864.22, 73/61.05, 61.55–61.61; 422/68.1, 70, 81, 422/99, 100, 103
See application file for complete search history.

(56) References Cited

U.S. PATENT DOCUMENTS

| 5,450,743 | A  | * | 9/1995 | Buote ......................... 73/61.56 |
| 5,797,719 | A  | * | 8/1998 | James et al. ..................... 417/46 |
| 6,652,755 | B2 | * | 11/2003 | Ikeda ............................ 210/662 |
| 7,219,566 | B1 | * | 5/2007 | Maeda ............................ 73/864 |
| 7,526,947 | B2 | * | 5/2009 | Tatsumi et al. ............... 73/61.55 |
| 2003/0042189 | A1 | * | 3/2003 | Shirota et al. ............... 210/198.2 |
| 2005/0191184 | A1 | * | 9/2005 | Vinson .......................... 417/44.2 |
| 2006/0027490 | A1 | * | 2/2006 | DeMarco ....................... 73/61.56 |
| 2006/0196282 | A1 | * | 9/2006 | Tatsumi et al. ............. 73/863.83 |
| 2008/0087547 | A1 | * | 4/2008 | Nakamura et al. ............. 204/600 |

FOREIGN PATENT DOCUMENTS

| CN | 1338628 | 3/2002 |
| JP | H10170488 | 6/1998 |
| JP | 2003215118 | 7/2003 |
| JP | 2006242720 | 9/2006 |

OTHER PUBLICATIONS

Chinese First Examination Report of China Application No. 200710166247.0, dated on Jul. 12, 2010.

* cited by examiner

*Primary Examiner* — Lisa M Caputo
*Assistant Examiner* — Punam Roy
(74) *Attorney, Agent, or Firm* — J.C. Patents

(57) ABSTRACT

An auto-sampler cleaning mechanism is provided, which is capable of maintaining the supply of a liquid in a non-time-consuming manner when a cleaning solution is supplied. The auto-sampler cleaning mechanism of the present invention includes: a sample-metering sample loop 14 having a sample-injecting needle 15 at a front end thereof, a metering pump 24, a multi-ported valve 11a, a multi-position valve 11b, and a liquid-supply valve 11c. A diaphragm pump 25 is disposed between the port of the multi-position valve 11a and the port of the liquid-supply valve 11b, and used to supply a cleaning solution 26 or a mobile phase 20 to the sample loop 14.

3 Claims, 2 Drawing Sheets

US 7,980,119 B2

AUTO-SAMPLER CLEANING MECHANISM

CROSS-REFERENCE TO RELATED APPLICATION

This application claims the priority benefit of Japan application serial no. 2006-328979, filed on Dec. 6, 2006. The entirety of the above-mentioned patent application is hereby incorporated by reference herein and made a part of this specification.

BACKGROUND OF THE INVENTION

1. Field of the Invention

The present invention relates a sample introduction device for introducing a sample into an analysis apparatus, such as liquid chromatograph. More particularly, the present invention relates to a total injection auto-sampler cleaning mechanism.

2. Description of Related Art

Total injection refers to a total amount of samples, taken from a sample bottle and metered by a sample needle, is completely injected from an injection port.

As for a sample introduction device capable of performing high precision metering regardless of the samples are micro samples or macro samples, it includes a metering pump and a multi-position valve. When a larger amount of samples is introduced, the samples are suctioned into a sample loop by switching the multi-position valve and performing the piston action back and forth by the metering pump (please refer to Japanese Patent Laid-Open Publication No. H10-170488).

Furthermore, if a larger amount of samples is introduced, the dead volume may increase occasionally. Therefore, a total injection liquid chromatograph has been proposed, in which the injection port is directly connected to a flow path switching valve without passing through any fitting pipe; thus, the dead volume and the retention volume of the flow path can be decreased (please refer to Japanese Patent Laid-Open Publication No. 2003-215118).

Furthermore, as for a total injection auto-sampler capable of injecting samples at a high metering precision even when a small amount of sample is introduced, an automatic sample introduction device with a function of automatically performing a sample pretreatment step has been proposed (please refer to Japanese Patent Laid-Open Publication No. 2006-242720).

Generally, a cleaning solution is supplied by a mechanism, including the pump of the metering portion or a syringe.

When a mechanism, for example, a pump or a syringe, is used to supply a liquid, in order to make the cleaning solution not flowing back during the suction and ejection process, a flow path switching valve is generally used to serve as a check valve. In this manner, as the cleaning solution cannot be supplied during the suction process, even if the amount of the supplied liquid is expected to increase, and time is only being consumed in the process of ejecting the liquid for the entire liquid-supply process.

Furthermore, when using a check valve, it is required to accurately stop the flow of the liquid in order to maintain the metering precision. However, in practice, there may exist a slight leakage of the liquid, and thus it is difficult to accurately stop the flow of the liquid.

SUMMARY OF THE INVENTION

Accordingly, the present invention is directed to an auto-sampler cleaning mechanism, capable of maintaining the supply of a liquid in a non-time-consuming manner when the liquid is supplied.

The auto-sampler cleaning mechanism of the present invention includes: a sample-metering sample loop, having a sample-injecting needle at a front end thereof; a metering pump; a multi-ported valve, having a port connected to the sample loop, a port connected to a column, and a port connected to a liquid supply pump, for switching the connections among the ports; a multi-position valve, having a port connected to the multi-ported valve through a flow path, a port connected to a flow path of supplying a mobile phase, a cleaning solution port, and a common port connected to the metering pump, for switching the connections between the common port and other ports; a liquid-supply valve, having a cleaning solution port connected to a flow path for supplying the cleaning solution, a port connected to the flow path for supplying the mobile phase or other mobile phases, and a common port for switching the connection to the common port; and a diaphragm pump, connected between the cleaning solution port of the multi-position valve and the common port of the liquid-supply valve. Furthermore, the diaphragm pump supplies the cleaning solution or the mobile phase to the sample loop.

In order to provide different cleaning solutions, the liquid-supply valve may have a plurality of ports.

In order to adjust the supply of the cleaning solution, the diaphragm pump is preferably connected to a pressure sensor and a control portion, which is used for controlling the diaphragm pump to supply a liquid.

Furthermore, when the voltage applied to the diaphragm pump is raised whereas the pressure of the pressure sensor is not increased, or when the applied voltage is dropped whereas the pressure value is not reduced, the control portion stops supplying a liquid.

EFFECTS OF THE INVENTION

According to the present invention, as a diaphragm pump is used when supplying the cleaning solution, the cleaning mechanism of the present invention is capable of maintaining the supply of the cleaning solution in a non-time-consuming manner, which is unlike the conventional pump or syringe mechanism.

Furthermore, when the liquid-supply valve at the upstream of the diaphragm pump has a plurality of ports for supplying more than two cleaning solutions, a plurality of cleaning solutions may be selected and supplied.

The diaphragm pump is generally used under a fixed voltage, but the flow of the supplied liquid cannot be controlled at this situation. Additionally, when the flow path has a relatively high resistance, the diaphragm pump may not supply the liquid. According to the present invention, the diaphragm pump has a control portion for monitoring the pressure applied to the flow path and maintaining the pressure within such a range that the diaphragm pump is capable of supplying the liquid. Thus, the liquid is maintained to be continuously supplied in a non-time-consuming manner, which is unlike the conventional pump or syringe mechanism.

In order to make the aforementioned and other objects, features and advantages of the present invention comprehensible, preferred embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Embodiments of the present invention are illustrated below.

Figure 1:
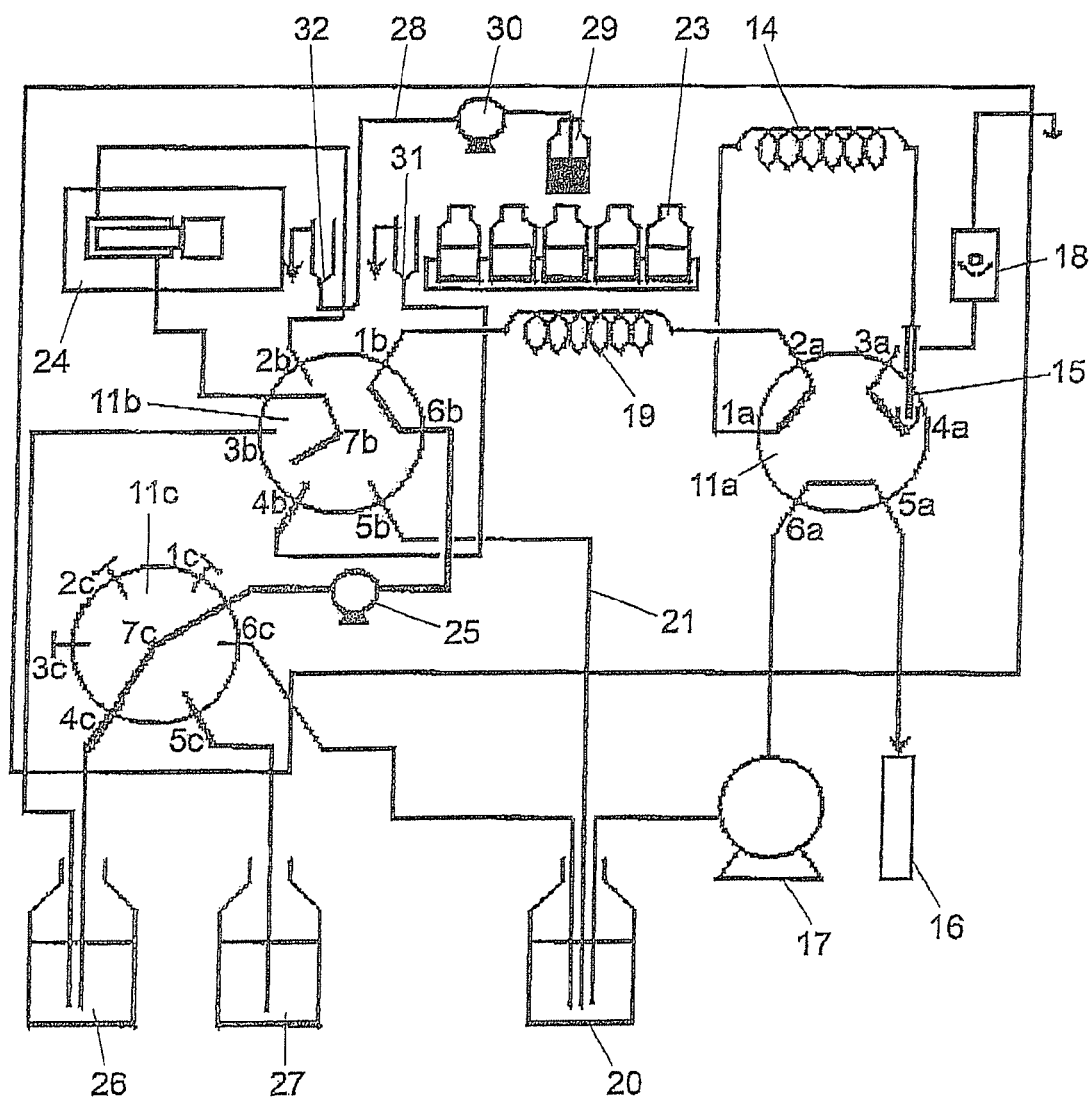
FIG. 1 is a general structural view of an auto-sampler cleaning mechanism.

FIG. 1 is a general structural view of an auto-sampler cleaning mechanism.

A sample loop 14 is connected to a port 1a of a multi-ported valve 11a hand has a sample-injecting needle 15 at a front end thereof. A port 5a of the valve 11a is connected to a column 16, and a port 6a of the valve 11a is connected to a pump 17.

A flow path 19 is disposed between a port 1b of a multi-position valve 11b and a port 2a of the valve 11a, such that a liquid with the same volume as the sample in the sample loop 14 may be stored. A port 5b of the valve 11b is connected to a mobile-phase-supply flow path 21 for the liquid supply pump 17 to supply a mobile phase 20. Furthermore, a port 2b of the valve 11b and a common port 7b of the valve 11b are connected to a metering pump 24 for metering the volume of the liquid.

A cleaning solution port 6b of the valve 11b is connected to a common port 7c of a liquid-supply valve 11c through a diaphragm pump 25. The diaphragm pump 25 will be described hereinafter.

A port 6c of the valve 11c is connected to the mobile phase 20, and a cleaning solution port 4c and a cleaning solution port 5c are respectively connected to cleaning solutions 26 and 27, and the liquid supplied to the diaphragm pump 25 is switched by switching the liquid-supply valve 11c.

A drain 31 is used to discharge the waste liquid that has been used for cleaning the sample loop 14.

A needle cleaning container 32 is connected to a cleaning solution 29 and a pump 30 through a flow path 28. The needle cleaning container 32 is disposed in a scope such that the needle 15 can be moved, so as to clean the outer portion of the needle 15. A sample bottle 23 is used to store the sample.

Furthermore, a port 3a of the valve 11a is connected to a stop joint (or a check valve) 18 to obstruct the flow.

Figure 2:
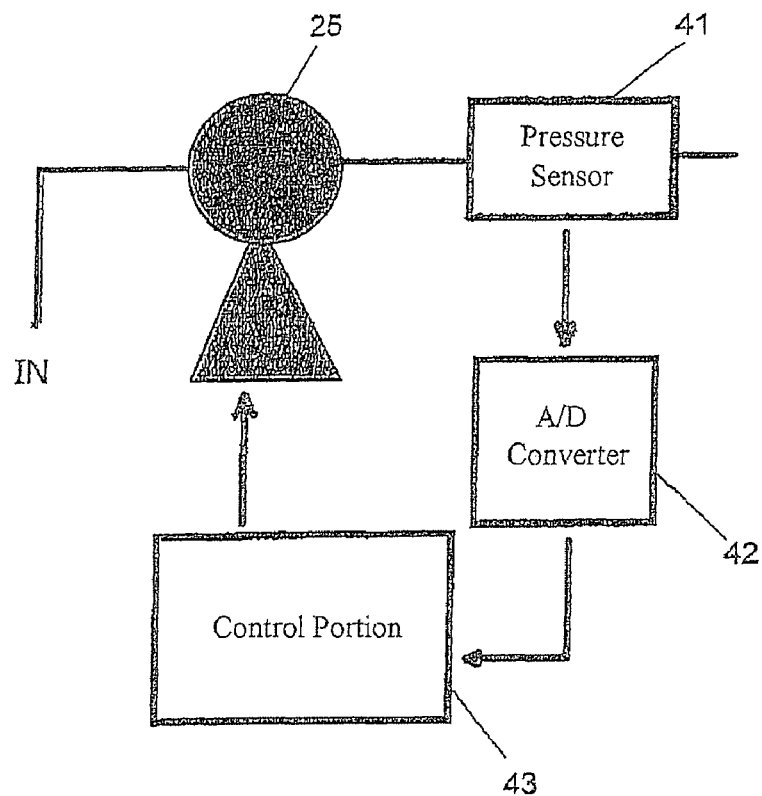
FIG. 2 is a block diagram of a diaphragm pump 25 and a control mechanism thereof.

FIG. 2 is a block diagram of a diaphragm pump 25 and a control mechanism thereof.

The diaphragm pump 25 is connected to a pressure sensor 41, an A/D converter 42, and a control portion 43 for controlling the liquid supply.

The pressure sensor 41 detects the liquid-supply pressure for the diaphragm pump 25. The detected pressure value is A/D converted by the converter 42 and then sent to the control portion 43.

Figure 3:
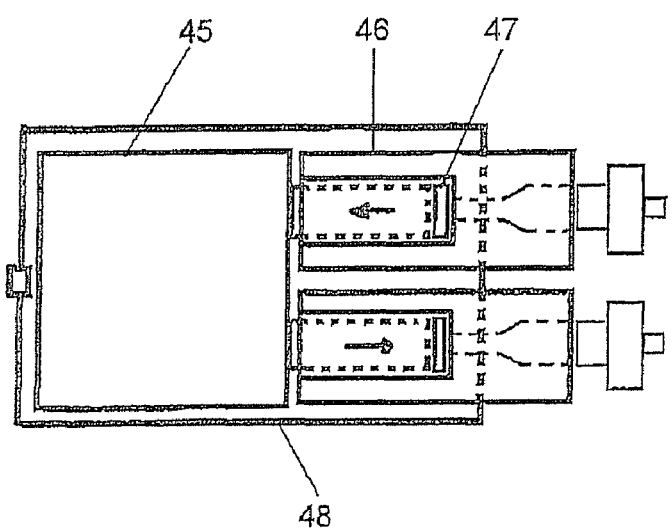
FIG. 3 is a general cross-sectional view of the diaphragm pump 25.

FIG. 3 is a general cross-sectional view of the diaphragm pump 25. The diaphragm pump body 45 is connected to two joints 46, and each of the joints 46 has a packing 47 at a portion connected with the liquid supply tube. The diaphragm pump body 25 and the joints 46 are connected by a joint-fixing band 48.

Furthermore, in order to prevent the liquid from leaking through the joints 46 when being supplied from the diaphragm pump 25, the following construction is adopted. That is, a resin packing 47 with high chemical resistance, for example, polytetrafluorethylene or polyethylene, is clamped between the joints 46 and the pumps; thus, they are clamped together firmly.

Next, referring to FIG. 1, the cleaning action in this embodiment is illustrated.

(1) The port 4c of the liquid-supply valve 11c is connected to the common port 7c. The port 6b of the multi-position valve 11b is connected to the port 1b. The port 1a of the multi-ported valve 11a is connected to the port 2a. In such a state, the diaphragm pump 25 is activated, such that the cleaning solution 26 is supplied to the sample loop 14 through the liquid-supply valve 11c, the multi-position valve 11b, the flow path 19, and the multi-ported valve 11a.

As the diaphragm pump 25 can supply the liquid continuously, even if there is a larger volume of a cleaning solution, the interior of the sample loop 14 still can be cleaned in a non-time-consuming manner. The cleaning solution may also clean other flow paths besides the sample loop 14.

(2) When a cleaning solution 27 is used, a selection may be performed by switching from the port 4c of the liquid-supply valve 11c to the port 5c. Furthermore, the unused ports are obstructed by the stop joint 18.

(3) When the interior of the metering pump 24 is cleaned, or it is required to ensure the volume of the cleaning solution to be accurate, the multi-position valve 11b is controlled. In this way, the cleaning solution may also be suctioned or ejected by the metering pump 24. For example, the cleaning solution 26 may be supplied to the metering pump 24 through the port 3b of the valve 11b.

(4) Furthermore, when the outer portion of the needle 15 is cleaned, the needle 15 may be moved to the needle cleaning container 32 with a cleaning solution stored therein for being cleaned, or the needle 15 may be immersed in an adjacent needle cleaning container 31 for being cleaned.

Next, referring to FIGS. 2 to 3, the action of the control mechanism for the diaphragm pump is described.

(1) At an initial use, the cleaning solution is supplied at a "Test Mode" to detect the voltage needed to be applied to the diaphragm pump 25 during the normal supplying and then the voltage value is stored. When supplying a cleaning solution, a voltage of the stored voltage value is applied as an initial voltage, which is monitored by a pressure sensor. Then, a proportional integral derivative (PID) control is performed on the applied voltage, so as to attain a fixed pressure.

(2) When the voltage applied to the diaphragm pump 25 is raised while the pressure is not increased, it is generally considered that a leakage occurs to the flow path, and thus an error is displayed, and the liquid supply is stopped.

(3) When the voltage applied to the diaphragm pump 25 is dropped while the pressure is not reduced, it is generally considered that the flow path is obstructed, and thus an error is displayed, and the liquid supply is stopped.

Furthermore, when performing an action of switching the valves, the pressure may be instantly raised sometimes, and thus at this time, no error is displayed.

Then, the action of injecting the sample is briefly described below.

When the sample is taken out of the sample bottle 23 and injected, the needle 15 is moved to the sample bottle 23, the sampled is suctioned by the metering pump 24, and the needle is moved to an injection port 4a, and then the multi-ported valve 11a is switched, so as to inject the sample.

The characteristics of this embodiments lie in that, a diaphragm pump is used when supplying the cleaning solution. However, in addition to the diaphragm pump, a liquid supply device capable of controlling the flow by controlling the applied voltage and having a function of high-flow liquid supply may also be used to supply the liquid.

INDUSTRIAL APPLICABILITY

The present invention can be applied in a sample introduction device for introducing a sample into an analysis apparatus, such as liquid chromatograph.

What is claimed is:

1. A cleaning method with an auto-sampler cleaning mechanism, the auto-sampler cleaning mechanism at least comprising:
    a sample-metering sample loop, having a sample-injecting needle at a front end thereof;
    a multi-ported valve;
    a multi-position valve;
    a liquid-supply valve;
    a diaphragm pump; and
    a pressure sensor and a control portion connected to the diaphragm pump for controlling the liquid supply of the diaphragm pump,
    the cleaning method comprising:
    connecting the sample-metering sample loop, the multi-ported valve, the multi-position valve, the diaphragm pump and the liquid-supply valve, so that a cleaning solution can be flowed through the liquid-supply valve, the diaphragm pump, the multi-position valve and the multi-ported valve to the sample-metering sample loop, and
    pumping the cleaning solution to the sample-metering sample loop by the diaphragm pump, wherein the control portion stops the liquid supply when a voltage applied to the diaphragm pump is raised but the pressure of the pressure sensor is not increased, or stops the liquid supply when a voltage applied to the diaphragm pump is dropped but the pressure is not reduced.

2. The cleaning method as claimed in claim 1, wherein the liquid-supply valve has a plurality of ports for supplying different cleaning solutions.

3. The cleaning method as claimed in claim 1, wherein the control portion monitors the pressure applied to the flow path and maintains the pressure within such a range that the diaphragm pump is capable of supplying the liquid, so that the liquid is maintained to be continuously supplied.

* * * * *